United States Patent [19]
Maier et al.

[11] Patent Number: 5,885,548
[45] Date of Patent: *Mar. 23, 1999

[54] MULTIPLY SUBSTITUTED DTPA DERIVATIVES AND THEIR METAL COMPLEXES, AND THEIR METAL COMPLEXES, PHARMACEUTICAL AGENTS THAT CONTAIN THESE COMPLEXES, THEIR USE IN DIAGNOSIS AND THERAPY, AS WELL AS PROCESS FOR THE PRODUCTION OF PHARMACEUTICAL AGENTS

[75] Inventors: Franz-Karl Maier; Michael Bauer; Werner Krause; Ulrich Speck; Gabriele Schuhmann-Giampiere, all of Berlin; Andreas Mühler, Neuenhagen; Thomas Balzer; Wolf-Rüdiger Press, both of Berlin, all of Germany

[73] Assignee: Schering Aktiengesellschaft, Germany

[*] Notice: This patent issued on a continued prosecution application filed under 37 CFR 1.53(d), and is subject to the twenty year patent term provisions of 35 U.S.C. 154(a)(2).

[21] Appl. No.: 565,024

[22] Filed: Nov. 30, 1995

Related U.S. Application Data

[63] Continuation-in-part of Ser. No. 387,408, Feb. 13, 1995, which is a continuation-in-part of Ser. No. 351,086, Nov. 30, 1994, abandoned.

[51] Int. Cl.⁶ .......................... A61B 5/055; A61K 49/04
[52] U.S. Cl. .................. 424/1.65; 424/9.364; 424/9.365; 424/9.42; 534/16; 556/50; 556/55; 556/63; 556/77; 556/134; 556/105; 556/116; 556/148
[58] Field of Search .......................... 424/9.364, 9.365, 424/9.42, 1.65; 128/653.4, 654; 436/173; 556/50, 55, 63, 77, 105, 116, 134, 148; 514/492, 502, 836; 534/16

[56] References Cited

U.S. PATENT DOCUMENTS

| | | | |
|---|---|---|---|
| 4,339,426 | 7/1982 | Meares et al. ........................ 424/1 |
| 4,622,420 | 11/1986 | Meares et al. ........................ 562/443 |
| 4,647,447 | 3/1987 | Gries et al. ........................ 424/9.36 |
| 4,652,519 | 3/1987 | Warshawsky et al. ............... 435/7 |
| 4,672,028 | 6/1987 | Olson ........................ 435/5 |
| 4,824,986 | 4/1989 | Gansow ........................ 558/17 |
| 4,880,008 | 11/1989 | Lauffer ........................ 128/654 |
| 4,899,755 | 2/1990 | Lauffer et al. ........................ 128/654 |
| 4,916,246 | 4/1990 | Felder ........................ 556/1 |
| 4,957,939 | 9/1990 | Gries et al. ........................ 514/492 |
| 4,963,344 | 10/1990 | Gries et al. ........................ 424/9 |
| 4,980,502 | 12/1990 | Felder et al. ........................ 562/444 |
| 5,021,236 | 6/1991 | Gries et al. ........................ 424/9 |
| 5,057,302 | 10/1991 | Johnson et al. ........................ 424/1.1 |
| 5,101,041 | 3/1992 | Troutner et al. ........................ 548/518 |
| 5,137,711 | 8/1992 | Weber et al. ........................ 424/9 |
| 5,182,370 | 1/1993 | Felder et al. ........................ 534/16 |
| 5,198,208 | 3/1993 | Berg et al. ........................ 424/1.1 |
| 5,250,285 | 10/1993 | Lauffer et al. ........................ 424/9 |
| 5,316,756 | 5/1994 | Gries et al. ........................ 424/9 |
| 5,318,771 | 6/1994 | Lauffer et al. ........................ 424/9 |
| 5,342,604 | 8/1994 | Wilson et al. ........................ 424/1.65 |
| 5,362,475 | 11/1994 | Gries et al. ........................ 424/9 |
| 5,399,340 | 3/1995 | Radüchel et al. ........................ 424/9 |
| 5,482,700 | 1/1996 | Deutsch et al. ........................ 424/9.364 |
| 5,695,739 | 12/1997 | Schmitt-Willich et al. ........... 424/9.42 |

FOREIGN PATENT DOCUMENTS

| | | |
|---|---|---|
| 0230893 | 8/1987 | European Pat. Off. . |
| 0405704 | 1/1991 | European Pat. Off. . |
| 0 450 742 | 4/1991 | European Pat. Off. . |
| 94/27644 | 12/1994 | WIPO . |
| 95/15319 | 6/1995 | WIPO . |

OTHER PUBLICATIONS

Havron A., Davis M. Seltzer S., Paskin–Hurlburt A., Hessel S. Heavy metal particulate contrast materials for computed tomography of the liver. J Comput Assist Tomogr 1980; 4:642–648.

Seltzer S, Douglas S F, Davis M, et al. Hepatic contrast agents for computed tomography: high atomic number particulate materials. J Comput Assist Tomogr 1981; 5:370–374.

Bloem J, Wondergem. Gd–DTPA as a contrast agent in CT. Radiology 1989; 171:578–579.

Zwicker C., Langer M., Urich V., Felix R. Kontrastgebung von jod, gadolinium und ytterbium in der CT. ROFO 1993; 158:255–259. (Abstract).

Schmitz SA, Wagner S, Schuhmann–Giampieri G, Wolf KJ. Evaluation of Gadobutrol in a rabbit model as new lanthanide contrast agent for computed tomography. Invest Radiol 1995; 30:644–649.

*Primary Examiner*—Gary E. Hollinden
*Attorney, Agent, or Firm*—Miller, White, Zelano, & Branigan, P.C.

[57] ABSTRACT

The invention relates to new, multiply substituted diethylenetriaminepentaacetic acid derivatives, their complexes and complex salts, that contain an element of atomic numbers 20-32, 39-51 or 57-83, pharmaceutical agents that contain these compounds, their use as contrast media and antidotes, and process for the production of pharmaceutical agents.

33 Claims, No Drawings

MULTIPLY SUBSTITUTED DTPA DERIVATIVES AND THEIR METAL COMPLEXES, AND THEIR METAL COMPLEXES, PHARMACEUTICAL AGENTS THAT CONTAIN THESE COMPLEXES, THEIR USE IN DIAGNOSIS AND THERAPY, AS WELL AS PROCESS FOR THE PRODUCTION OF PHARMACEUTICAL AGENTS

This application is a continuation-in-part of Ser. No. 08/387,408, filed Feb. 13, 1995, which in turn is a continuation-in-part of Ser. No. 08/351,086 filed Nov. 30, 1994 abandoned. Ser. No. 08/487,094 filed Jun. 6, 1995, is also a continuation-in-part of Ser. No. 08/387,408 filed Feb. 13, 1995, and Ser. No. 08/480,566 filed Jun. 7, 1995, is a divisional of Ser. No. 08/487,094. The entirety of each of the above-identified applications is hereby incorporated by reference.

SUMMARY OF THE INVENTION

The invention relates to novel, multiply substituted DTPA (diethylenetriaminepentaacetic acid) derivatives and their metal complexes, pharmaceutical agents that contain these complexes and their use in diagnosis and therapy.

Contrast media are indispensable additives in modern diagnosis; thus many diseases could not be diagnosed without the use of contrast media. Contrast media are used in all areas of diagnosis, such as, e.g., diagnostic radiology, radiodiagnosis or ultrasound diagnosis or magnetic resonance imaging (MRI or NMR imaging)

The selection of the method preferred in each case depends, i.a., on the diagnostic problem, but is also determined by the choice of apparatus available in each case to the physician. Thus, because of the considerable technical expenditure and associated high cost, in particular magnetic resonance imaging has not yet found the wide use of other methods, such as, e.g., methods of diagnostic radiology.

The selection of the suitable contrast medium also varies on the basis of the respective problem. Thus, the suitability of the contrast medium for a specific object is determined last but not least by its concentration and distribution behavior in the organism.

Although great progress has been achieved both on the equipment side and on the contrast medium side, solutions satisfactory for all problems are not yet available.

Thus, suitable contrast media do not exist for all indications for the various imaging processes. In particular, until now, no suitable x-ray contrast medium for liver diagnosis has been available.

In diagnostic radiology, basically contrast media based on triiodobenzene have been able to gain acceptance, since these compounds exhibit a high x-ray opacity, a low general and local toxicity and are very readily water-soluble.

Such compounds are described, e.g., in EP 0 105 752 and EP 0 015 867. But, the latter show insufficient concentration in the liver for a diagnostic x-ray imaging.

The radio-opaque effect of an x-ray contrast medium is basically dependent on the size of the mass attenuation coefficient of the elements, contained in the compound, in the diagnostic range of radiation. In addition to iodine-containing compounds, complexes of metals of higher atomic numbers are also suitable as x-ray contrast media. Physiologically compatible complex compounds of these metals are already widely used in the field of NMR diagnosis. In general, these are metal complexes, as they are described, e.g., in EP 0 071 564.

WO 93/16375 describes metal complexes, which are linked by amide bonds to iodine-substituted aromatic compounds. These compounds are intended to allow both NMR and x-ray investigations to be performed with only one administration of contrast medium. A combination of the two imaging processes is advantageous in many cases for a differentiated visualization and a reliable determination of certain diseases. These compounds are to be suitable especially for angiography. As the reprocessing of the production samples reveals, however, the compounds show insufficient concentration in the area of the liver for X-ray investigations.

An object of the invention is therefore to make available new chemical compounds that are suitable for the production of very well-tolerated and water-soluble contrast media for diagnostic radiology, NMR diagnosis and radiodiagnosis or radiotherapy—especially for diagnostic radiology of the liver.

Upon further study of the specification and appended claims, further objects and advantages of this invention will become apparent to those skilled in the art.

These objects are achieved by the substances, agents and methods described below.

It has been found that metal complexes of general formula I

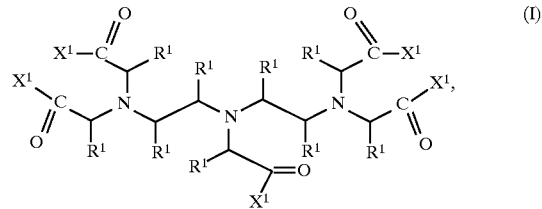

in which
5, 6 or 7 of the radicals referred to with $R^1$ stand for hydrogen and the other radicals, independently of one another, stand for a radical of formula Ia

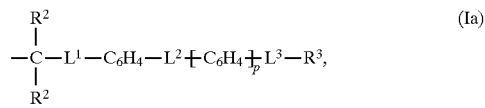

in which
p stands for number 0 or 1,
$R^2$, independently of one another, in each case stands for a hydrogen atom or a branched or unbranched, saturated or unsaturated hydrocarbon $C_1$–$C_6$ radical,
$R^3$ stands for a hydrogen atom or a branched or unbranched, saturated or unsaturated $C_1$–$C_6$ hydrocarbon radical or a carboxyl group,
$L^1$ stands for a direct bond, a sulfur atom, a $C_1$–$C_4$ alkylene chain or $L^1$ stands for a $C_1$–$C_4$ alkylene chain that is interrupted by a sulfur atom,
$L^2$ and $L^3$, respectively independently of one another, each stand for a direct bond, an oxygen atom, a sulfur atom or a $C_1$–$C_{10}$ alkylene chain, which optionally is interrupted by one to three oxygen atoms and/or one to three sulfur atoms,
wherein in $L^2$—$[C_6H_4]_p$—$L^3$ two or more heteroatoms are not directly bonded to one another and
$X^1$, independently of one another, in each case stands for a group O—$X^2$ or N($R^4$)$R^5$,
$R^4$ and $R^5$, independently of one another, stand for a hydrogen atom, $C_1$–$C_6$ alkyl or for a radical $R^1$ or R$^4$ and R$^5$ together, with inclusion of the common amide nitrogen atom, form a four- to eight-membered ring, which can in addition optionally contain up to two oxygen atoms and/or up to two carbonyl or sulfonyl groups, X$^2$, independently of one another, in each case stands for a hydrogen atom or a metal ion equivalent of an element of atomic numbers 20-32, 39-51 or 57-83, as well as salts thereof with physiologically compatible inorganic and/or organic cations for, for example, charge neutralization, are very well suited for the production of contrast media for diagnostic radiology and/or NMR diagnosis and/or radiodiagnosis, preferably contrast media for diagnostic radiology, especially for diagnostic radiology of the liver, the bile ducts and the gallbladder.

The invention therefore relates to the compounds of general formula I.

Compounds of general formula I in which all occurring radicals X$^2$ have the meaning of hydrogen atoms are referred to as complexing agents or as ligands. Compounds of general formula I, in which at least one of the contained heteroatoms (oxygen, nitrogen or sulfur) is bound in a coordinated manner to a metal atom, are referred to as complexes.

Compounds of general formula I, in which at least two of the contained heteroatoms (oxygen, nitrogen or sulfur) are bound in a coordinated manner to the same metal atom, are referred to as chelate complexes.

If the metal complex according to the invention is intended for the production of agents for diagnostic radiology, the central ion must be derived from an element of a higher atomic number to achieve a sufficient absorption of the x rays. It has been found that elements of atomic numbers 57-83 are especially suitable for this purpose. Quite especially suitable are complexes of the elements lanthanum, gadolinium, terbium, dysprosium, holmium, erbium, ytterbium, lutetium, bismuth, lead and hafnium.

If the metal complex according to the invention is intended for the production of agents for NMR diagnosis, the central ion must be paramagnetic. It has been found that for this purpose, especially the chromium(III), iron(II), cobalt(II), nickel(II), copper(II), praseodymium(III), neodymium(III), samarium(III) and the ytterbium(III) ions are suitable. Especially preferred are complexes of the ions gadolinium(III), terbium(III), dysprosium(III), holmium (III), erbium(III), iron(III) and manganese(II).

If the metal complex according to the invention is intended for the production of agents for nuclear medicine, the central ion must be radioactive. Suitable are, for example, the radioisotopes of the elements copper, cobalt, gallium, germanium, yttrium, strontium, technetium, indium, ytterbium, gadolinium, samarium, silver, gold, rhenium, bismuth and iridium. Preferred radioisotopes are gallium-67, indium-111 and technetium-99m.

Suitable C$_1$–C$_6$ hydrocarbon radicals for R$^2$ and R$^3$ include methyl, ethyl, isopropyl, propyl, butyl, vinyl, phenyl, and cyclohexyl. The compounds according to the invention can contain, as groups of formula —C(=O)X$^1$, carboxylates (—CO$_2$X$^2$) or carboxylic acid amides (—C(=O)N(R$^4$)R$^5$). Radicals R$^4$ and R$^5$, independently of one another, can be hydrogen atoms or radicals of formula R$^1$. Suitable are, for example, compounds in which one or two of the carboxylic acid groups that are present in the molecule are present as alkylamides (for example, methyl-, ethyl-, propyl- or butylamides). Also suitable are compounds in which one or two of the carboxylic acid groups that are present in the molecule are present as benzylamides or their derivatives, for example, methoxybenzylamide, ethoxybenzylamide, propoxybenzylamide, butoxybenzylamide, benzyloxybenzylamide, methylbenzylamide, ethylbenzylamide, propylbenzylamide, butylbenzylamide or benzylbenzylamide.

Radicals R$^4$ and R$^5$ can also together form, for example, a C$^3$–C$^7$ alkylene chain which, together with inclusion of the amide nitrogen atom, forms a four- to eight-membered ring, which can contain zero to two additional oxygen atoms and/or zero to two additional carbonyl or sulfonyl groups. If R$^3$ and R$^4$ together stand for a ring system, the morpholine ring or the S,S-dioxothiomorpholine ring are preferred.

As radicals R$^1$ of general formula I, lipophilic radicals that are described by formula Ia are used. Particularly, those radicals that contain aromatic groups or are interrupted by aromatic groups exhibit advantageous properties. Radicals R$^1$ can also contain heteroatoms, such as nitrogen, oxygen or sulfur, in which two heteroatoms are not connected with one another. In particular, substituted benzyl radicals can be used as radicals R$^1$, such as, for example, methoxybenzyl, ethoxybenzyl, propoxybenzyl, butoxybenzyl, pentoxybenzyl, benzyloxybenzyl, methylbenzyl, ethylbenzyl, propylbenzyl, butylbenzyl, pentylbenzyl and benzylbenzyl radicals. Especially suitable is the butylbenzyl radical. Radicals R$^1$ can also contain several heteroatoms, such as, for example, (ethoxy)-ethoxybenzyl, 2-(2-ethoxyethoxy)-ethoxybenzyl, 2-(methoxy)ethoxybenzyl and ((ethoxy)ethoxy)methoxybenzyl radicals; preferred is the ethoxybenzyl radical. The benzyl radicals can be substituted in 2-, 3- or 4-position, i.e., in ortho, meta or para position. Substituents in ortho and para position are preferred in this case, quite especially preferred are radicals in para position.

2, 3 or 4 of the radicals referred to with R$^1$ can stand for a group of formula Ia. Remaining radicals R$^1$ in each case stand for a hydrogen atom. Each of the radicals R$^1$ which are not hydrogen can be the same or different within a molecule.

Well suited are those compounds in which two of radicals R$^1$ in each case stand for a radical of formula Ia. Extremely well suited are those compounds in which two of radicals R$^1$ in each case stand for an alkoxybenzyl radical. Especially suitable are those compounds in which two of radicals R$^1$ in each case stand for an ethoxybenzyl radical.

Those compounds in which 3 or 4 of radicals R$^1$ stand for an ethoxybenzyl radical also exhibit excellent properties.

For the above-mentioned commercial uses, the following complexing agents are especially well suited:

3,6,9-Triaza-3,9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid, 3,6,9-triaza-3,6,9-tris-(carboxymethyl)-4,8-bis-(4-ethoxybenzyl)-undecanedioic acid, 3,6,9-triaza-3,6,9-tris-(carboxymethyl)-2,10-bis-(4-ethoxybenzyl)-undecanedioic acid, 3,6,9-triaza-3,9-bis-(carboxymethyl)-6-{2-[4-(carboxymethoxy)-phenyl]-1-carboxyethyl}-4-[4-propoxybenzyl]-undecanedioic acid, 3,6,9-triaza-6-(carboxymethyl)-3,9-bis-[2-(4-methoxyphenyl)-1-carboxyethyl]-2,10-bis-(4-methoxybenzyl)-undecanedioic acid, 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid and 3,6,9-triaza-3,6,9-tris-(carboxymethyl)-2,10-bis-(4-ethoxybenzyl)-4,8-bis-(4-propoxybenzyl)-undecanedioic acid.

For the production of pharmaceutical agents, the following complexes also exhibit excellent properties:

Bismuth complex of 3,6,9-triaza-3,9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid, ytterbium complex of 3,6,9-triaza-3,6,9-tris-(carboxymethyl)-4,8-bis-(4-ethoxybenzyl)-undecanedioic acid, gadolinium complex of 3,6,9-triaza-3,6,9-tris-(carboxymethyl)-2,10-bis-(4-ethoxybenzyl)-undecanedioic acid, hafnium complex of 3,6,9-triaza-3,9-bis-(carboxymethyl)-6-{2-[4-(carboxymethoxy)-phenyl]-1-carboxyethyl}-4-[4-propoxybenzyl]-undecanedioic acid, terbium complex of 3,6,9-triaza-6-(carboxymethyl)-3,9-bis-[2-(4-methoxyphenyl)-1-carboxyethyl]-2,10-bis-(4-methoxybenzyl)-undecanedioic acid, holmium complex of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid and erbium complex of 3,6,9-triaza-3,6,9-tris-(carboxymethyl)-2,10-bis-(4-ethoxybenzyl)-4,8-bis-(4-propoxybenzyl)-undecanedioic acid as well as their salts and amides.

It is often the case that the complexing agent exhibits more acid functions than the complexed metal has positive elementary charges. Thus, for example, the 3,6,9-triaza-3,6,9-tris-(carboxymethyl)-2,10-bis-(4-ethoxybenzyl)-undecanedioic acid described in Example 3 has five acid groups, while the gadolinium in the gadolinium oxide ($Gd_2O_3$) is present in oxidation stage +III. In the case of complexing, thus only three of the five protons of the acid are neutralized. A complex which contains two protons that can be dissociated, an acid complex, is thus formed. In aqueous solution, two protons and one dianion—formed from the metal and the complexing agent—are thus present. For many purposes, it is advantageous to exchange the protons for other physiologically compatible cations (neutralization), so that a salt is formed. As physiologically compatible cations, sodium$^+$, calcium$^{2+}$, magnesium$^{2+}$ and zinc$^{2+}$ as well as cations of organic bases, such as meglumine, glucosamine, arginine, ornithine, lysine and ethanolamine, can be mentioned as examples.

Production of the Complexes According to the Invention

Production of the complexes according to the invention can take place, for example, in the way disclosed in patent specifications EP 71564, EP 130934 and DE-OS 3401052, by a metal oxide or a metal salt (for example, a chloride, nitrate, acetate, carbonate or sulfate) of the element of atomic numbers 20-32, 39-51 or 57-83 being dissolved or suspended in water and/or another polar solvent (such as methanol, ethanol, isopropanol or N,N-dimethylformamide) and reacted with a solution or suspension of the equivalent amount of a complexing agent of general formula II

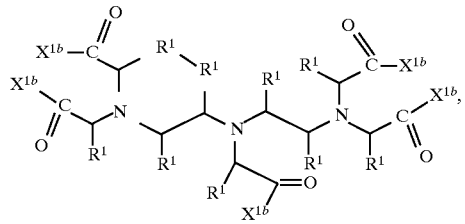

in which $R^1$ has the above-mentioned meanings, $X^{1b}$, independently of one another, in each case stands for a group HO or $N(R^4)R^5$ with $R^4$ and $R^5$ having the above-mentioned meanings, and then, if desired, existing acid hydrogen atoms of acid groups can be substituted by cations of inorganic and/or organic bases or amino acids.

In this case, the neutralization takes place with the help of inorganic bases (e.g., hydroxides, carbonates or bicarbonates of, e.g., sodium, calcium or lithium) and/or organic bases, such as, i.a., primary, secondary and tertiary amines, such as, e.g., ethanolamine, glucamine, N-methylglucamine and N,N-dimethylglucamine, as well as basic amino acids, such as, e.g., lysine, arginine and ornithine.

For the production of neutral complex salts, enough of the desired bases can be added, for example, to the acid complex salts in aqueous solution or suspension so that the neutral point is reached. The obtained solution can then be evaporated to dryness in a vacuum. Often, it is advantageous to precipitate the formed neutral salts by the addition of water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

If the acid complexes contain several free acid groups, it is often suitable to produce neutral mixed salts, which contain both inorganic and organic cations as counterions.

This can happen, for example, by reacting the complexing agents in aqueous suspension or solution with the oxide or salt of the desired element and half of the amount of an organic base required for neutralization. The formed complex salt can then be isolated optionally purified and then mixed with the required amount of inorganic base for complete neutralization. The sequence of the addition of bases can also be reversed.

Another possibility to arrive at neutral complex compounds involves converting the remaining acid groups, as described, e.g., in EP 0450742, completely or partially to amides.

If the agents according to the invention are to contain radioisotopes, the production of the complexes from the complexing agents can take place according to the methods described in "Radiotracers for Medical Applications," Vol. I, CRC Press, Boca Raton, Fla.

Production of the Complexing Agents According to the Invention

The production of the compounds of general formula I generally takes place by cleavage of the acid protective groups consisting of compounds of general formula III

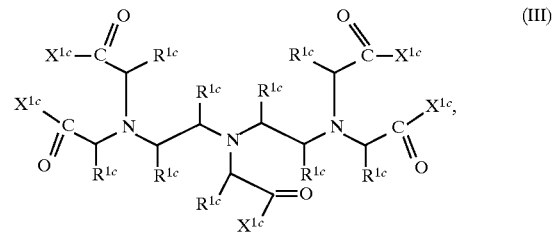

in which 5, 6 or 7 of the radicals referred to with $R^{1c}$ stand for hydrogen and the other radicals, independently of one another, stand for a radical of formula Ia, in which optionally present carboxyl groups are present in protected form, $X^{1c}$, independently of one another, in each case stands for a group ZO or $N(R^4)R^5$ with $R^4$ and $R^5$ having the above-mentioned meanings, in which Z has the meaning of an acid protective group.

The acid protective groups and process for their cleavage are well known to one skilled in the art or can be found in relevant literature (e.g.: Protective Groups in Organic Syntheses, Second Edition, T. W. Greene and P. G. M. Wuts, John Wiley & Sons, Inc., New York, 1991).

Possibilities for the production of the compounds of general formula III are known to one skilled in the art. Actual embodiments of production processes are described in the examples. One skilled in this field has extensive technical knowledge as to how these processes can be modified to be able to obtain the compounds desired in each case.

Additional information about reaction processes and reaction conditions is published in the following publications:

Synthesis of ethers, in particular phenolic ethers:
Houben-Weyl, Band VI/3, Teil A, Georg Thieme Verlag, Stuttgart, 1965
Synthesis of amines and amino acid derivatives:
Houben-Weyl, Band XI/1, Georg Thieme Verlag, Stuttgart, 1957,
Houben-Weyl, Band XI/2, Georg Thieme Verlag, Stuttgart, 1958
Synthesis of alkyl halides:
Houben-Weyl, Band V/3, Georg Thieme Verlag, Stuttgart, 1962
Houben-Weyl, Band V/4, Georg Thieme Verlag, Stuttgart, 1960
Synthesis of carboxylic acids and derivatives thereof:
Houben-Weyl, Band VIII, Georg Thieme Verlag, Stuttgart, 1952
Synthesis of sulfonic acid derivatives:
Houben-Weyl, Band IX, Georg Thieme Verlag, Stuttgart, 1955
Reductive amination:
C. F. Lane, Synthesis 135 (1975)
Synthesis of DTPA derivatives"
M. A. Williams, H. Rapport, J. Org. Chem., 58, 1151 (1993)

Pharmaceutical Agents

Another object of the invention are agents, which contain at least one of the compounds according to the invention as well as a process for the production of these agents, which is characterized in that the chelate complex is dissolved in water and put into a form that is suitable for enteral or parenteral administration with the additives and stabilizers usual in galenicals, so that the chelate complex is present in a concentration of preferably about 1 to 1500 mmol/l, especially in a concentration of about 10 to 1000 mmol/l. Often, it is advantageous for the pharmaceutical agent to contain small additions (about 0.1 to 10 mole % relative to the diagnostically effective metal complex) of complexing agents. In a like manner, it can be advantageous if the pharmaceutical agent contains small additions (0.1 to 10 mole % relative to the diagnostically effective metal complex) of metal complexes of weakly bound metals. In particular, sodium, calcium, magnesium and zinc complexes are suitable as additives in this regard. They can be used in the form of complexes with the complexing agents according to the invention, but also in the form of metal complexes with other complexing agents, such as DTPA, EDTA (ethyleneediaminetetraacetic acid), TTHA (triethyleneediaminetetraacetic acid) and derivatives of the latter. The resulting agents are then optionally sterilized. They are administered generally in a dose of about 1 to 300 ml on the basis of the diagnostic problem.

Suitable additives are, for example, physiologically harmless buffers (such as, e.g., tromethamine), small additions of complexing agents (such as, e.g., diethylenetriaminepentaacetic acid) or, if necessary, electrolytes, such as, e.g., sodium chloride or, if necessary, antioxidants, such as, e.g., ascorbic acid.

If suspensions or solutions of the agents according to the invention in water or physiological salt solution are desired for enteral administration or other purposes, they are mixed with one or more adjuvants usual in galenicals (e.g., methyl cellulose, lactose, mannitol), and/or surfactants (e.g., lecithins, Tweens®, Myrj®) and/or flavoring substances for taste correction (e.g., ethereal oils).

In principle, it is also possible to produce the diagnostic agents according to the invention even without isolating the complex salts. In each case, special care must be used to undertake the chelation, so that the salts and salt solutions according to the invention are practically free of noncomplexed metal ions having a toxic effect.

This can be assured, for example, with the help of color indicators, such as xylenol orange, by control titrations during the production process. The invention therefore also relates to a process for the production of complex compounds and their salts. A purification of the isolated complex salt remains as a final precaution.

The substances according to the invention meet the varied requirements which are to be imposed for contrast media in modern diagnosis. The compounds and agents produced from them are distinguished by:

an unprecedented physiological compatibility of the metal complexes according to the invention,
a high absorption coefficient for X-rays with the use of metals cited for this purpose,
an excellent relaxivity with the use of the mentioned paramagnetic metals,
a high effectiveness, which is necessary to load the body with the smallest possible amounts of foreign substances,
a good water solubility (this allows for the production of highly-concentrated solutions, as needed especially for use as X-ray contrast media. Thus, the volume load of the circulatory system is kept within reasonable limits),
a low viscosity,
low osmolality,
advantageous excretion kinetics.

Further, the agents according to the invention exhibit not only a high stability in vitro, but also a surprisingly high stability in vivo, so that a release or an exchange of ions—toxic in themselves—not covalently bound to the complexes does not take place within the time in which the new contrast media are completely excreted again.

In addition to the high water solubility, which, surprisingly, was able to be increased to a range suitable for diagnostic radiology, the complex compounds according to the invention have a positive effect in diagnostic radiology in that they surprisingly permit investigations with shorter-wave X-ray radiation than that which is possible with conventional contrast media, by which the radiation exposure of the patient is clearly reduced, since, as is generally known, soft radiation of tissue is much more greatly absorbed than hard (R. Felix, Das Röntgenbild [The X-Ray Image]; Thieme Stuttgart 1980).

For use in diagnostic radiology, the complexes of the following metals according to the invention are especially suitable: gadolinium, terbium, dysprosium, holmium, erbium, ytterbium, lutetium, bismuth, lead and hafnium.

Because of the advantageous absorption properties of the contrast media according to the invention in the area of hard X-ray radiation, the agents are also especially suitable for digital subtraction techniques (which work with higher tube voltages).

It is further to be emphasized that the compounds according to the invention are distinguished by an improved heart/circulatory system compatibility in comparison with other complex compounds.

The surprisingly advantageous in vivo distribution behavior of the agents according to the invention is especially to be emphasized. This permits, for the first time, with a low dose for X-ray contrast media (about 0.1–1 mmol/kg of body weight), the production of X-ray pictures of high diagnostic informative value in the area of the liver, as well as of the bile ducts and the gallbladder, particularly in the case of use in computer tomography.

In addition to use in diagnostic radiology, the agents according to the invention, which contain in the complex a paramagnetic metal ion can also be used in NMR diagnosis. This dual nature opens up further fields of use. Thus, these agents according to the invention can be used advantageously if a combination of diagnostic radiology and NMR diagnosis is necessary for differentiated visualization and reliable determination of certain diseases. This is true, e.g., in the case of suspicion of recurrence after tumor operations or radiation therapy. In these cases, the patient is spared an additional load by double administration by using a contrast medium which is equally suitable for both techniques.

The complexing agents and their complexes according to the invention with weakly bound metals (e.g., $Na^+$, $Ca^{2+}$, $Mg^{2+}$, and $Zn^{2+}$) are, moreover, suitable to remove heavy metals from the body, for example, after a heavy metal poisoning. In particular, a detoxification of the liver is possible by the extrarenal excretion of the complexing agents and complexes according to the invention. The use of the compounds according to the invention for the production of agents for treating heavy metal poisonings, especially for treating heavy metal poisonings of the liver, are therefore also an object of the invention.

Additional objects of the invention are characterized by the claims.

In general, it has been possible with the mentioned complex compounds to open up new possibilities in diagnostic and therapeutic medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

The following examples are used for a more detailed explanation of the objects of the invention without intending to be limiting.

Example 1

Bismuth complex of the disodium salt of 3,6,9-triaza-3, 9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid a) N-Benzyloxycarbonyl-3-[4-(1,4,7-trioxaoctyl)-phenyl]-alanine-methyl ester 6.59 g (20 mmol) of N-benzyloxycarbonyl-tyrosine-methyl ester is dissolved in 25 ml of anhydrous N,N-dimethylformamide and mixed at 0° C. under argon with 0.81 g (20.5 mmol) of sodium hydride dispersion (60% in mineral oil). The batch is allowed to stir for 10 minutes, then 3.75 g (20.5 mmol) of 1-bromo-2-(2-methoxyethoxy)-ethane is added, the reaction temperature is allowed to increase to room temperature and stirred for another three hours. For working-up, the batch is taken up in toluene and shaken out several times against aqueous sodium bicarbonate solution. The organic phase is separated, dried on magnesium sulfate, filtered and concentrated by evaporation. The oily residue is chromatographed for purification on silica gel with hexane/diethyl ether/triethylamine.

Yield: 7.6 g (88% of theory) of colorless oil.

Analysis (relative to solventless substance):

Cld: C 64.02 H 6.77 N 3.25 O 25.96 Fnd: C 64.13 H 6.59 N 3.11 b) N-Benzyloxycarbonyl-2-amino-2-[4-(1,4,7-trioxaoctyl)-benzyl]-ethanol 7.35 g (17 mmol) of N-benzyloxycarbonyl-3-[4-(1,4,7-trioxaoctyl)-phenyl]-alanine-methyl ester (Example a) is dissolved in 35 ml of tert-butyl methyl ether and mixed with 0.9 g (23.8 mmol) of sodium borohydride. At 5° C., 10 ml of methanol is added, and it is stirred for four hours under argon at constant temperature. Then, 1.5 ml of acetic acid, dissolved in 5 ml of tetrahydrofuran, is added, mixed with 5 ml of water and stirred for ten minutes at room temperature. The organic phase is separated, washed with water and dried on sodium sulfate. The drying agent is suctioned off, the filtrate is concentrated by evaporation and the residue is chromatographed for purification on silica gel.

Yield: 6.4 g (93.3% of theory)

Analysis (relative to solventless substance):

Cld: C 65.49 H 7.24 N 3.47 O 23.79 Fnd: C 65.34 H 7.32 N 3.36 c) 2-Amino-2-[4-(1,4,7-trioxaoctyl)-benzyl]-ethanol 6.3 g (15.6 mmol) of the compound produced according to Example b) is dissolved in 35 ml of ethanol and after the addition of 0.6 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 4.1 g (97.6% of theory)

Analysis (relative to solventless substance):

Cld: C 62.43 H 8.61 N 5.20 O 23.76 Fnd: C 62.26 H 8.67 N 5.04 d) N-{2-Hydroxy-1-[4-(1,4,7-trioxaoctyl)-benzyl]-ethyl}-iminodiacetic acid-di-tert-butyl ester 3.9 g (14.5 mmol) of the compound described in Example c), 6.2 g (32 mmol) of bromoacetic acid-tert-butyl ester and 4.4 g (32 mmol) of potassium carbonate are stirred in 15 ml of tetrahydrofuran/water (2:1) for two days at 65° C. After cooling, it is filtered, concentrated by evaporation in a vacuum, and the residue is chromatographed on silica gel with diethyl ether/hexane/triethylamine. The product fractions are concentrated by evaporation in a vacuum and dried.

Yield: 6.1 g (84.5% of theory)

Analysis (relative to solventless substance):

Cld: C 62.76 H 8.71 N 2.82 O 25.72 Fnd: C 62.59 H 8.88 N 2.80 e) N-{2-Bromo-1-[4-(1,4,7-trioxaoctyl)-benzyl]-ethyl}-iminodiacetic acid-di-tert-butyl ester A solution of 5.8 g (11.6 mmol) of the compound described in Example d) and 3.35 g (12.8 mmol) of triphenylphosphine in 50 ml of dichloromethane is mixed at 0° C.

in portions with 2.28 g (12.8 mmol) of N-bromosuccinimide and then stirred for 20 hours at room temperature. The solution is concentrated by evaporation and the residue is absorptively precipitated with tert-butyl methyl ether. A precipitate develops, which is separated and washed with tert-butyl methyl ether. The combined filtrates are concentrated by evaporation and the residue is chromatographed on silica gel with hexane/diethyl ether. The concentration by evaporation of the product fractions yields a colorless oil.

Yield: 5.9 g (90.7% of theory)
Analysis (relative to solventless substance):
Cld: C 55.71 H 7.55 Br 14.26 N 2.50 O 19.98 Fnd: C 55.62 H 7.39 Br 14.14 N 2.38 f) N-Benzyloxycarbonyl-3-[4-(1,4,7-trioxaoctyl)-phenyl]-alanine-tert-butyl ester 7.43 g (20 mmol) of N-benzyloxycarbonyl-tyrosine-tert-butyl ester is reacted with 1-bromo-2-(2-methoxyethoxy)-ethane to alkylated phenol analogously to Example a).

Yield: 8.2 g (86.6% of theory) of colorless oil.
Analysis (relative to solventless substance):
Cld: C 65.94 H 7.45 N 2.96 O 23.65 Fnd: C 65.98 H 7.52 N 2.78 g) 3-[4-(1,4,7-Trioxaoctyl)-phenyl]-alanine-tert-butyl ester 7.9 g (16.7 mmol) of the compound produced according to Example f) is dissolved in 40 ml of ethanol and after the addition of 0.8 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 5.5 g (97.0% of theory)
Analysis (relative to solventless substance):
Cld: C 63.69 H 8.61 N 4.13 O 23.57 Fnd: C 63.57 H 8.71 N 4.05 h) 3,6,9-Triaza-3,9-bis-(tert-butoxycarbonylmethyl)-6-{2-[4-(1,4,7-trioxaoctyl)-phenyl]-1-tert-butoxycarbonylethyl}-4,8-bis-[4-(1,4,7-trioxaoctyl)-benzyl]-undecanedioic acid-di-tert-butyl ester 5.2 g (15.3 mmol) of the amine produced according to Example g) and 18.9 g (33.7 mmol) of the bromide produced according to Example e) is introduced into 65 ml of acetonitrile and mixed with 30 ml of 2N phosphate buffer solution (pH 8.0). The batch is vigorously stirred at room temperature for 30 hours, and the aqueous phosphate buffer phase is exchanged for fresh buffer solution after 2, 8 and 18 hours. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 16.3 g (82.0% of theory) of colorless oil.
Analysis (relative to solventless substance):
Cld: C 64.74 H 8.62 N 3.24 O 23.41 Fnd: C 64.58 H 8.70 N 3.29 i) Bismuth complex of the disodium salt of 3,6,9-triaza-3,9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid 15.9 g (12.2 mmol) of the compound produced according to Example h) is dissolved in 65 ml of tetrahydrofuran and mixed with 75 ml of 2N sodium hydroxide solution, it is stirred for four hours at 55° C., adjusted to pH 1.3 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained.

The penta acid is taken up in 250 ml of water and mixed with 6.22 g (12.2 mmol) of bismuth oxycarbonate. The suspension is stirred for 25 hours at 100° C. and filtered. Then, it is adjusted to pH 7.2 with 1N sodium hydroxide solution. Then, after the addition of 1.6 g of activated carbon, the solution is stirred for one hour at 60° C. and filtered. After freeze-drying, the filtrate yields a colorless solid.

Yield: 14.7 g (95% of theory)
Analysis (relative to anhydrous substance):
Cld: C 47.36 H 5.25 N 3.31 O 23.97 Bi 16.48 Na 3.63 Fnd: C 47.21 H 5.44 N 3.26 Bi 16.27 Na 3.29

Example 2

Ytterbium complex of the disodium salt of 3,6,9-triaza-3,6,9-tris-(carboxymethyl)-4,8-bis-(4-ethoxybenzyl)-undecanedioic acid a) 2-(4-Ethoxybenzyl)-2-aminoethanol 45.0 g (136.7 mmol) of [2-(4-ethoxyphenyl)-1-hydroxyphenyl)-ethyl]-carbaminic acid benzyl ester (DE 4302287 A1), dissolved in 300 ml of ethanol, is mixed with 3.0 g of palladium (10%) on activated carbon and it is hydrogenated until hydrogen absorption is completed. Then, catalyst is filtered out, and the filtrate is evaporated to dryness.

Yield: 26.7 g (100% of theory) of colorless solid.
Analysis (relative to solventless substance):
Cld: C 69.28 H 7.04 N 4.25 O 19.43 Fnd: C 69.25 H 7.11 N 4.13 b) N,N-[1-(4-Ethoxybenzyl)-2-hydroxyethyl]-iminodiacetic acid-di-tert-butyl ester 20 g (102.4 mmol) of 2-(4-ethoxybenzyl)-2-aminoethanol (Example a) is reacted with 40 g (205 mmol) of bromoacetic acid-tert-butyl ester analogously to Example 1d). After chromatographic purification, the dialkylation product is obtained as colorless oil.

Yield: 37.6 g (86.7% of theory)
Analysis (relative to solventless substance):
Cld: C 65.22 H 8.81 N 3.31 O 22.66 Fnd: C 65.07 H 8.92 N 3.28 c) N,N-[2-Bromo-1-(4-ethoxybenzyl)-ethyl]-iminodiacetic acid-di-tert-butyl ester By reaction of 9.3 g (21.9 mmol) of the diester of Example b) with triphenylphosphine and N-bromosuccinimide analogously to Example 1e), the bromide is obtained as pale yellow oil.

Yield: 8.9 g (83.5% of theory)
Analysis (relative to solventless substance):
Cld: C 56.79 H 7.46 Br 16.43 N 2.88 O 16.44 Fnd: C 56.63 H 7.50 Br 16.29 N 2.69 d) 3,6,9-Triaza-3,6,9-tris-(tert-butoxycarbonylmethyl)-4,8-bis-(4-ethoxybenzyl)-undecanedioic acid-di-tert-butyl ester 1.4 g (8.5 mmol) of glycine-tert-butyl ester hydrochloride and 8.5 g (17.5 mmol) of the bromide produced according to Example c) are introduced into 45 ml of acetonitrile and mixed with 20 ml of 2N phosphate buffer solution (pH 8.0). The batch is vigorously stirred at room temperature for 28 hours, and the aqueous phosphate buffer phase is exchanged for fresh buffer solution after 2, 8 and 16 hours. Then, the organic phase is concentrated by evaporation in a vacuum and the residue is chromatographed on silica gel. The product-containing fractions are concentrated by evaporation in a vacuum.

Yield: 5.3 g (66.2% of theory) of colorless oil.
Analysis (relative to solventless substance):
Cld: C 66.29 H 8.88 N 4.46 O 20.38 Fnd: C 66.37 H 8.79 N 4.33 e) Ytterbium complex of the disodium salt of 3,6,9-triaza-3,6,9-tris-(carboxymethyl)-4,8-bis-(4-ethoxybenzyl)-undecanedioic acid 4.7 g (5 mmol) of the penta-tert-butyl ester (Example d) is dissolved in 25 ml of tetrahydrofuran and mixed with 20 ml of 2N sodium hydroxide solution, it is stirred for two hours at 50° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and dried under high vacuum, by which the free ligand is obtained.

The penta acid is taken up in 100 ml of water and mixed with 1.31 g (2.5 mmol) of ytterbium carbonate. The suspension is stirred for two hours at 60° C. and filtered. Then, it is adjusted to pH 7.2 with 1N sodium hydroxide solution. Then, after the addition of 0.5 g of activated carbon, the solution is stirred at 50° C. for one hour and filtered. After freeze-drying, the filtrate yields a colorless solid.

Yield: 4.1 g (94% of theory)
Analysis (relative to anhydrous substance):
Cld: C 43.89 H 4.37 N 4.80 O 21.92 Yb 19.76 Na 5.26
Fnd: C 43.71 H 4.47 N 4.63 Yb 19.58 Na 4.96

Example 3

Gadolinium complex of the disodium salt of 3,6,9-triaza-3,6,9-tris-(carboxymethyl)-2,10-bis-(4-ethoxybenzyl)-undecanedioic acid a) 3,6,9-Triaza-2,10-bis-(4-ethoxybenzyl)-undecanedioic acid-diisopropyl ester, trihydrochloride 10.4 g (50 mmol) of α-oxo-4-ethoxyphenylacetic acid (Bandyopahyay et al., J. Ind. Chem. Soc. 66(4), 239, 1989) is dissolved in 55 ml of methanol and reacted with 2.58 g (25 mmol) of diethylenetriamine. After six hours at 60° C., it is allowed to cool to room temperature and 0.76 g (20 mmol) of sodium borohydride is added. It is allowed to stir overnight and then the reaction mixture is mixed carefully with diluted hydrochloric acid until no more gas generation can be observed. The reaction mixture is concentrated by evaporation and dried in an oil pump vacuum for several hours at 100° C. The residue is taken up in isopropanol. Hydrogen chloride gas is introduced until saturation is achieved, stirred for two hours at room temperature and then for eight hours at 85° C. Then, it is concentrated by evaporation, the residue is dispersed between ethyl acetate and sodium bicarbonate solution, the organic phase is dried on sodium sulfate, filtered and concentrated by evaporation. In the solution of the residue in tert-butyl methyl ether, hydrogen chloride gas is introduced until saturation is achieved, and the settled precipitate is suctioned off.

Yield: 13.7 g (80.4% of theory) of pale yellow solid.
Analysis (relative to solventless substance):
Cld: C 56.43 H 7.70 Cl 15.62 N 6.17 O 14.09 Fnd: C 56.51 H 7.61 Cl 15.29 N 6.30 b) 3,6,9-Triaza-3,6,9-tris-(tert-butoxycarbonylmethyl)-2,10-bis-(4-ethoxybenzyl)-undecanedioic acid-diisopropyl ester 13.3 g (19.5 mmol) of diester of Example a) is reacted with 12.57 g (64.4 mmol) of bromoacetic acid-tert-butyl ester analogously to Example 1d).

After chromatographic purification, the title compound is obtained as colorless oil.

Yield: 14.6 g (81.9% of theory)
Analysis (relative to solventless substance):
Cld: C 65.69 H 8.71 N 4.60 O 21.00 Fnd: c 65.53 H 8.84 N 4.50 c) Gadolinium complex of the disodium salt of 3,6,9-triaza-3,6,9-tris-(carboxymethyl)-2,10-bis-(4-ethoxybenzyl)-undecanedioic acid 14.2 g (15.5 mmol) of the compound produced according to Example b) is dissolved in 45 ml of tetrahydrofuran and mixed with 55 ml of 2N sodium hydroxide solution, it is stirred for three hours at 55° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained. The penta acid is taken up in 120 ml of water and mixed with 2.81 g (7.77 mmol) of gadolinium oxide. The suspension is stirred for 7 hours at 90° C. and filtered. Then, it is adjusted to pH 7.1 with 1N sodium hydroxide solution. Then, after the addition of 1.4 g of activated carbon, the solution is stirred at 70° C. for one hour and filtered. The filtrate is freeze-dried.

Yield: 12.4 g (93% of theory) of colorless solid.
Analysis (relative to anhydrous substance):
Cld: C 44.70 H 4.45 N 4.89 O 22.33 Gd 18.29 Na 5.35
Fnd: C 44.56 H 4.52 N 4.81 Gd 18.14 Na 5.09

Example 4

Hafnium complex of the disodium salt of 3,6,9-triaza-3,9-bis-(carboxymethyl)-6-{2-[4-(carboxymethoxy)-phenyl]-1-carboxyethyl}-4-[4-propoxybenzyl]-undecanedioic acid a) N-Benzyloxycarbonyl-3-[4-propoxyphenyl]-alanine-methyl ester 4.94 g (15 mmol) of N-benzyloxycarbonyl-tyrosine-methyl ester is dissolved in 25 ml of anhydrous N,N-dimethylformamide and mixed at 5° C. under argon with 0.61 g (15.5 mmol) of sodium hydride dispersion (60% in mineral oil). The batch is allowed to stir for 10 minutes, then 1.91 g (15.5 mmol) of propyl bromide is added, the reaction temperature is allowed to increase to room temperature and it is stirred for another two hours. For working-up, the batch is taken up in ethyl acetate and shaken out several times against aqueous sodium bicarbonate solution. The organic phase is separated, dried on magnesium sulfate, filtered and concentrated by evaporation. The residue is chromatographed for purification on silica gel with hexane/diethyl ether/triethylamine.

Yield: 4.3 g (74.7% of theory) of colorless oil.
Analysis (relative to solventless substance):
Cld: C 67.91 H 6.78 N 3.77 O 21.54 Fnd: C 67.78 H 6.64 N 3.83 b) N-Benzyloxycarbonyl-2-amino-2-[4-propoxybenzyl]-ethanol 4.15 g (11.2 mmol) of N-benzyloxycarbonyl-3-[4-propoxyphenyl]-alanine-methyl ester is dissolved in 20 ml of tert-butyl methyl ether and mixed with 0.17 g (4.5 mmol) of sodium borohydride. At 0° C., 6 ml of methanol is added and it is stirred for three hours under argon at a temperature below 5° C. Then, 0.8 ml of acetic acid, dissolved in 3 ml of tetrahydrofuran, is added, mixed with 3 ml of water and stirred for ten minutes at room temperature. The organic phase is separated, washed with water and dried on sodium sulfate. The drying agent is suctioned off, the filtrate is concentrated by evaporation and the residue is chromatographed for purification on silica gel (eluent: ethyl acetate/hexane).

Yield: 3.55 g (92.3% of theory)
Analysis (relative to solventless substance):
Cld: C 69.95 H 7.34 N 4.08 O 18.64 Fnd: C 69.74 H 7.42 N 3.96 c) 2-Amino-2-[4-propoxybenzyl]-ethanol 3.4 g (10 mmol) of the Z-protected amine of Example b) is hydrogenated under palladium catalysis analogously to Example 1c).

Yield: 2.0 g (96.5% of theory) of colorless oil.
Analysis (relative to solventless substance):
Cld: C 68.87 H 9.15 N 6.69 O 15.29 Fnd: C 69.02 H 9.08 N 6.47 d) N-[1-(4-Propoxybenzyl)-2-hydroxyethyl]-iminodiacetic acid-di-tert-butyl ester 1.9 g (9.1 mmol) of the amine of Example c) is reacted with 3.9 g (20 mmol) of bromoacetic acid-tert-butyl ester analogously to Example 1d). After chromatographic purification on silica gel, the dialkylation product is obtained as colorless oil.

Yield: 3.6 g (90.4% of theory)
Analysis (relative to solventless substance):
Cld: C 65.88 H 8.98 N 3.20 O 21.94 Fnd: C 65.97 H 9.06 N 3.14 e) N-[2-Bromo-1-(4-propoxybenzyl)-ethyl]-iminodiacetic acid-di-tert-butyl ester

From 3.4 g (7.77 mmol) of the diester of Example d) and triphenylphosphine and N-bromosuccinimide, the bromide is obtained as yellow oil analogously to Example 1e).

Yield: 3.25 g (83.6% of theory)
Analysis (relative to solventless substance):
Cld: C 56.60 H 7.65 Br 15.97 N 2.80 O 15.98 Fnd: C 56.51 H 7.47 Br 16.04 N 2.64 f) N-Benzyloxycarbonyl-3-[4-(tert-butoxycarbonylmethoxy)-phenyl]-alanine-tert-butyl ester 5.57 g (15 mmol) of N-benzyloxycarbonyl-tyrosine-tert-butyl ester is reacted with bromoacetic acid-tert-butyl ester to alkylated phenol analogously to Example 1a).

Yield: 6.1 g (83.7% of theory) of colorless oil.
Analysis (relative to solventless substance):
Cld: C 66.79 H 7.26 N 2.88 O 23.06 Fnd: C 66.62 H 7.17 N 2.81 g) N-[N',N'-Bis-(tert-butoxycarbonylmethyl)-2-aminoethyl]-N-benzyloxycarbonyl-3-[4-(tert-butoxycarbonylmethoxy)-phenyl]-alanine-tert-butyl ester 5.9 g (12.1 mmol) of the amine of Example f) is mixed in 20 ml of N,N-dimethylformamide at 0° C. with 0.56 g (14.0 mmol) of sodium hydride. After 15 minutes, 4.69 g (13.3 mmol) of N,N-bis-[(tert-butoxycarbonyl)-methyl]-2-bromoethylamine (M. Williams and H. Rapoport, J. Org. Chem. 58, 1151 (1993)) is added and stirring of the batch is allowed to continue overnight at room temperature. Then, the organic phase is shaken out with tert-butyl methyl ether/sodium bicarbonate solution, the tert-butyl methyl ether phase is dried on sodium sulfate and filtered. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 6.9 g (75.3% of theory) of yellowish oil.
Analysis (relative to solventless substance):
Cld: C 65.06 H 7.99 N 3.70 O 23.25 Fnd: C 65.20 H 8.14 N 3.53 h) N-[N',N'-Bis-(tert-butoxycarbonylmethyl)-2-aminoethyl]-3-[4-(tert-butoxycarbonylmethoxy)-phenyl]-alanine-tert-butyl ester 6.75 g (8.9 mmol) of the benzyloxycarbonyl-protected amine (Example g) is hydrogenated with the addition of 0.7 g of palladium (10%) on activated carbon at normal pressure and room temperature. After hydrogen absorption is completed, the catalyst is filtered out and the filtrate is evaporated to dryness.

Yield: 5.5 g (99.2% of theory) of colorless oil.
Analysis (relative to solventless substance):
Cld: C 63.64 H 8.74 N 4.50 O 23.12 Fnd: C 63.49 H 8.87 N 4.63 i) 3,6,9-Triaza-3,9-bis-(tert-butoxycarbonylmethyl)-6-{2-[4-(tert-butoxycarbonylmethoxy)-phenyl]-1-(tert-butoxycarbonyl)-ethyl}-4-[4-propoxybenzyl]-undecanedioic acid-di-tert-butyl ester 5.2 g (8.3 mmol) of the amine produced according to Example h) and 4.36 g (8.7 mmol) of the bromide obtained according to Example e) are dissolved in 35 ml of acetonitrile and mixed with 15 ml of 2N phosphate buffer solution (pH 8.0). The batch is vigorously stirred at room temperature for 36 hours, and the aqueous phosphate buffer phase is exchanged for fresh buffer solution after 2, 8 and 24 hours. Then, the organic phase is concentrated by evaporation in a vacuum and the residue is chromatographed on silica gel with hexane/diethyl ether/triethylamine. The product-containing fractions are concentrated by evaporation in a vacuum.

Yield: 7.6 g (87.8% of theory) of yellowish oil.
Analysis (relative to solventless substance):
Cld: C 65.68 H 8.80 N 4.03 O 21.49 Fnd: C 65.54 H 8.91 N 3.89 j) 3,6,9-Triaza-3,9-bis-(carboxymethyl)-6-{2-[4-(carboxymethoxy)-phenyl]-1-carboxyethyl}-4-[4-propoxybenzyl]-undecanedioic acid 7.3 g (7 mmol) of the hexaester of Example i) is dissolved in 35 ml of methanol and stirred with 20 ml of 2N sodium hydroxide solution at 70° C. for five hours. Then, the methanol is distilled off, taken up in water and precipitated with concentrated hydrochloric acid. The solid is suctioned off, washed neutral with water and the ligands are dried at 50° C. in a vacuum.

Yield: 4.36 g (88.3% of theory) of colorless solid.
Analysis (relative to solventless substance):
Cld: C 56.17 H 6.14 N 5.95 O 31.74 Fnd: C 56.03 H 6.01 N 6.13 k) Hafnium complex of the disodium salt of 3,6,9-triaza-3,9-bis-(carboxymethyl)-6-{2-[4-(carboxymethoxy)-phenyl]-1-carboxyethyl}-4-[4-propoxybenzyl]-undecanedioic acid 4.2 g (6 mmol) of hexa acid of Example j) is suspended in 120 ml of water and mixed with 1.47 g (6 mmol) of hafnium hydroxide (D. J. Williams et al., J. Chem. Soc. Dalton Trans. 2475, 1992). The reaction solution is stirred for 36 hours at 100° C. After complexing is completed, it is filtered, concentrated by evaporation to about half the prior volume, and freeze-dried.

Yield: 5.1 g (92% of theory) of colorless lyophilizate.
Analysis (relative to anhydrous substance):
Cld: C 42.89 H 4.04 N 4.55 O 24.24 Hf 19.31 Na 4.98 Fnd: C 42.76 H 4.20 N 4.41 Hf 19.13 Na 4.72

Example 5

Terbium complex of the disodium salt of 3,6,9-triaza-6-(carboxymethyl)-3,9-bis-[2-(4-methoxyphenyl)-1-carboxyethyl]-2,10-bis-(4-methoxybenzyl)-undecanedioic acid a) 3-[4-Methoxyphenyl]-alanine-tert-butyl ester 7.12 g (30 mmol) of tyrosine-tert-butyl ester is dissolved in 28 ml of anhydrous N,N-dimethylformamide and mixed at 5° C. under argon with 1.21 g (31 mmol) of sodium hydride dispersion (60% in mineral oil). The batch is allowed to stir for 15 minutes, then 4.4 g (31 mmol) of methyl iodide is added, the reaction temperature is allowed to increase to room temperature and it is stirred for another hour. For working-up, the batch is taken up in ethyl acetate and shaken out several times against aqueous sodium bicarbonate solution. The organic phase is separated, dried on magnesium sulfate, filtered and concentrated by evaporation. The residue is chromatographed for purification on silica gel with hexane/diethyl ether/triethylamine.

Yield: 6.8 g (90.2% of theory) of colorless oil.
Analysis (relative to solventless substance):
Cld: C 66.91 H 8.42 N 5.57 O 19.10 Fnd: C 66.98 H 8.55 N 5.33 b) 3-[4-Methoxyphenyl]-2-bromo-propionicacid-tert-butyl ester 6.55 g (26.1 mmol) of the amino acid ester of Example a) is converted to the corresponding bromide analogously to the method of A. Spaltenstein, et al. (THL 34, p. 1457, 1993). After chromatographic purification on silica gel, the product is obtained as pale yellow solid.
Yield: 6.4 g (77.8% of theory)
Analysis (relative to solventless substance):
Cld: C 53.35 H 6.08 Br 25.35 O 15.23 Fnd: C 53.24 H 5.97 Br 25.21 c) N-(2-Hydroxyethyl)-2,4-bis-(4-methoxybenzyl)-3-azaglutaric acid-di-tert-butyl ester 6.2 g (20 mmol) of the bromide of Example b) is dissolved at 0° C. in 15 ml of N,N-dimethylformamide and mixed with 2.2 g (22 mmol) of potassium bicarbonate. Then, 0.54 g (8.9 mmol) of ethanolamine is added, stirred for 30 minutes at low temperature and then for three days at room temperature. The batch is mixed with 100 ml of tert-butyl methyl ether, extracted with saturated sodium bicarbonate solution and saturated common salt solution, and the organic phase is dried on sodium sulfate. After the filtration, it is evaporated to dryness.
Yield: 5.8 g (49% of theory) of colorless oil, which slowly crystallizes completely.
Analysis (relative to solventless substance):
Cld: C 68.03 H 8.18 N 2.64 O 21.14 Fnd: C 67.76 H 8.23 N 2.88 d) N-(2-Bromoethyl)-2,4-bis-(4-methoxybenzyl)-3-azaglutaric acid-di-tert-butyl ester From 5.6 g (10.6 mmol) of the diester of Example c) and triphenylphosphine and N-bromosuccinimide, the bromide is obtained as pale yellow oil analogously to Example 1e).
Yield: 5.12 g (81.5% of theory)
Analysis (relative to solventless substance):
Cld: C 60.81 H 7.14 Br 13.48 N 2.36 O 16.20 Fnd: C 60.70 H 7.08 Br 13.29 N 2.44 e) 3,6,9-Triaza-6-(tert-butoxycarbonylmethyl)-3,9-bis-[2-(4-methoxyphenyl)-1-(tert-butoxycarbonyl)-ethyl]-2,10-bis-(4-methoxybenzyl)-undecanedioic acid-di-tert-butyl ester 4.85 g (8.2 mmol) of the bromide produced according to Example d) and 0.67 g (4 mmol) of glycine-tert-butyl ester-hydrochloride are introduced into 35 ml of acetonitrile and mixed with 20 ml of 2N phosphate buffer solution (pH 8.0). The batch is vigorously stirred at room temperature for 30 hours, and the aqueous phosphate buffer phase is exchanged for fresh buffer solution after 2 and 18 hours. Then, the organic phase is concentrated by evaporation in a vacuum, and the residue is chromatographed on silica gel with hexane/diethyl ether/triethylamine. The product-containing fractions are concentrated by evaporation in a vacuum.
Yield: 4.1 g (88.8% of theory) of colorless oil.
Analysis (relative to solventless substance):
Cld: C 68.66 H 8.29 N 3.64 O 19.40 Fnd: C 68.73 H 8.31 N 3.50 f) Terbium complex of the disodium salt of 3,6,9-triaza-6-(carboxymethyl)-3,9-bis-[2-(4-methoxyphenyl)-1-carboxyethyl}-2,10-bis-(4-methoxybenzyl)-undecanedioic acid 3.9 g (3.4 mmol) of the pentaester produced according to Example e) is dissolved in 15 ml of tetrahydrofuran and mixed with 15 ml of 2N sodium hydroxide solution, it is stirred for three hours at 55° C., adjusted to pH 1 with concentrated hydrochloric acid, greatly concentrated by evaporation in a rotary evaporator and the residue is purified by ion exchange chromatography (cationic exchanger ($H^+$ form), eluent: ammonia-water solution). The eluate is concentrated by evaporation and greatly dried under high vacuum, by which the free complexing agent is obtained. The penta acid is taken up in 100 ml of water and mixed with 0.85 g (1.7 mmol) of terbium carbonate hydrate. The suspension is stirred for 15 hours at 70° C. and filtered. Then, it is adjusted to pH 7.1 with 1N sodium hydroxide solution. Then, after the addition of 0.4 g of activated carbon, the solution is stirred at 90° C. for one hour and filtered. After freeze-drying, the filtrate yields a colorless solid.
Yield: 3.4 g (93.1% of theory)
Analysis (relative to anhydrous substance):
Cld: C 51.45 H 4.69 N 3.91 O 20.86 Tb 14.80 Na 4.28 Fnd: C 51.27 H 4.73 N 3.76 Tb 14.68 Na 3.94

Example 6

Holmium complex of the disodium salt of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid a) N-Benzyl-N-(2-hydroxyethyl)-glycine-tert-butyl ester 15.1 g (100 mmol) of N-benzylethanolamine is dissolved in 50 ml of tetrahydrofuran and mixed with 15 ml of water and 13.8 g (100 mmol) of potassium carbonate. After instillation of 20.5 g (105 mmol) of bromoacetic acid-tert-butyl ester, it is stirred for 6 hours at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.
Yield: 24.8 g (93.3% of theory) of colorless oil.
Analysis (relative to solventless substance):
Cld: C 67.90 H 8.74 N 5.28 O 18.09 Fnd: C 67.87 H 8.88 N 5.19 b) N-Benzyl-N-(2-bromoethyl)-glycine-tert-butyl ester

A solution of 20 g (75.4 mmol) of the compound described under a) and 22.9 g (87.1 mmol) of triphenylphosphine in 400 ml of dichloromethane is mixed at 0° C. in portions with 15.5 g (87.1 mmol) of N-bromosuccinimide and then stirred for 20 hours at room temperature. The solution is concentrated by evaporation and the residue is absorptively precipitated with tert-butyl methyl ether. A precipitate develops, which is separated and washed with tert-butyl methyl ether. The combined filtrates are concentrated by evaporation and the residue is chromatographed on silica gel with hexane/diethyl ether. The concentration by evaporation of the product fractions yields a colorless oil.
Yield: 20.3 g (81.7% of theory) of colorless oil.
Analysis (relative to solventless substance):
Cld: C 54.89 H 6.76 Br 24.34 N 4.27 O 9.75 Fnd: C 54.77 H 6.81 Br 24.12 N 4.34 c) 2,4-Bis-(4-hydroxybenzyl)-3-azaglutaric acid-diisopropyl ester 9.01 g (50.0 mmol) of 4-hydroxyphenylpyruvic acid and 9.06 g (50.0 mmol) of tyrosine are dissolved in 60 ml of methanol and stirred for six hours at 60° C. Then, it is allowed to cool to room temperature and 0.76 g (20 mmol) of sodium borohydride is added. It is allowed to stir overnight and then the reaction mixture is mixed carefully with diluted hydrochloric acid until no more gas generation can be observed. The reaction mixture is concentrated by evaporation and dried in an oil pump vacuum for several hours at 100° C. The residue is taken up in isopropanol. Hydrogen chloride gas is introduced until saturation is achieved, stirred for two hours at room temperature and then for eight hours at 85° C. Then, it is concentrated by evaporation, the residue is dispersed between ethyl acetate and sodium bicarbonate solution, the organic phase is dried on sodium sulfate, filtered and concentrated by evaporation. The residue is chromatographed on silica gel with use of hexane/ethyl acetate as mobile solvent. The fractions that contain the pure product are combined and concentrated by evaporation.

Yield: 16.0 g (74.5% of theory) of pale yellow oil.
Analysis (relative to solventless substance):
Cld: C 67.11 H 7.28 N 3.26 O 22.35 Fnd: C 67.04 H 7.33 N 3.16 d) N-(3-Aza-3-benzyl-4-tert-butoxycarbonyl-butyl)-2,4-bis-(4-hydroxybenzyl)-3-azaglutaric acid-diisopropyl ester 10.8 g (33.0 mmol) of the compound produced according to Example b) and 12.9 g (30 mmol) of the compound described in Example c) are introduced into 45 ml of acetonitrile and mixed with 25 ml of 2N phosphate buffer solution (pH 8.0). The batch is vigorously stirred at room temperature for 22 hours, and the aqueous phosphate buffer phase is exchanged for fresh buffer solution after 2 and 7 hours. Then, the organic phase is concentrated by evaporation in a vacuum and the residue is chromatographed on silica gel with hexane/ethyl acetate/triethylamine. The product-containing fractions are concentrated by evaporation in a vacuum.

Yield: 13.9 g (68.3% of theory) of colorless oil.
Analysis (relative to solventless substance):
Cld: C 69.21 H 7.74 N 4.14 O 18.91 Fnd: C 69.13 H 7.78 N 4.16 e) N-(3-Aza-3-benzyl-4-tert-butoxycarbonyl-butyl)-2,4-bis-(4-methoxybenzyl)-3-azaglutaric acid-diisopropyl ester 12.5 g (18.5 mmol) of the compound described in Example d) is dissolved in 50 ml of anhydrous N,N-dimethylformamide and mixed at 0° C. under argon with 1.60 g (40.0 mmol) of sodium hydride dispersion (60% in mineral oil). The batch is allowed to stir for 15 minutes, then 6.81 g (48.0 mmol) of methyl iodide is added, the reaction temperature is allowed to increase to room temperature and it is stirred for another four hours. For working-up, the batch is taken up in toluene and shaken out several times against aqueous sodium bicarbonate solution. The organic phase is separated, dried on magnesium sulfate, filtered and concentrated by evaporation. The oily residue is chromatographed on silica gel with hexane/diethyl ether/triethylamine, the product-containing fractions are combined and concentrated by evaporation.

Yield: 11.6 g (89.2% of theory) of colorless oil.
Analysis (relative to solventless substance):
Cld: C 69.86 H 8.01 N 3.97 O 18.16 Fnd: C 69.78 H 8.23 N 3.78 f) N-(3-Aza-4-tert-butoxycarbonyl-butyl)-2,4-bis-(4-methoxybenzyl)-3-azaglutaric acid-diisopropyl ester 11.0 g (15.5 mmol) of the compound produced according to Example e) is dissolved in 50 ml of ethanol and after the addition of 1.0 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 9.35 g (97.5% of theory)
Analysis (relative to solventless substance):
Cld: C 66.43 H 8.20 N 4.56 O 20.82 Fnd: C 66.54 H 8.33 N 4.46 g) N-[3-Aza-4-tert-butoxycarbonyl-3-(2-hydroxyethyl)-butyl]-2,4-bis-(4-methoxybenzyl)-3-azaglutaric acid-diisopropyl ester 8.99 g (14.6 mmol) of the compound described in Example f) is dissolved in 30 ml of tetrahydrofuran and mixed with 2 ml of water and 2.02 g (14.6 mmol) of potassium carbonate. After instillation of 2.2 g (17.5 mmol) of bromoethanol, it is stirred for 6 hours at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 7.84 g (81.4% of theory) of colorless oil.
Analysis (relative to solventless substance):
Cld: C 65.63 H 8.26 N 4.25 O 21.86 Fnd: C 65.78 H 8.40 N 4.11 h) N-[3-Aza-4-tert-butoxycarbonyl-3-(2-bromoethyl)-butyl]-2,4-bis-(4-methoxybenzyl)-3-azaglutaric acid-diisopropyl ester A solution of 7.73 g (11.7 mmol) of the compound described under Example g) and 3.39 g (12.9 mmol) of triphenylphosphine in 50 ml of dichloromethane is mixed at 0° C. in portions with 2.30 g (12.9 mmol) of N-bromosuccinimide and then stirred for 20 hours at room temperature. The solution is concentrated by evaporation and the residue is absorptively precipitated with hexane. A precipitate develops, which is separated and washed with hexane. The combined filtrates are concentrated by evaporation and the residue is chromatographed on silica gel with hexane/diethyl ether. The concentration by evaporation of the product fractions yields a colorless oil.

Yield: 7.07 g (83.5% of theory) of colorless oil.
Analysis (relative to solventless substance):
Cld: C 59.91 H 7.40 Br 11.07 N 3.88 O 17.74 Fnd: C 60.04 H 7.52 Br 10.89 N 3.95 i) N-Benzyl-tyrosine-tert-butyl ester 16.9 g (71.5 mmol) of tyrosine-tert-butyl ester and 8.33 g (78.6 mmol) of benzaldehyde are stirred in 50 ml of methanol for 3 hours at 24° C. and then mixed with 3.37 g (53.6 mmol) of sodium cyanoborohydride. After 24 hours of stirring at room temperature, the batch is adjusted to pH 2 by careful addition of semiconcentrated hydrochloric acid, then neutralized with concentrated aqueous sodium bicarbonate solution and after substantial evaporation of methanol with ethyl acetate, it is shaken out. The organic phase is dried on anhydrous magnesium sulfate, filtered and concentrated by evaporation. The residue is chromatographed on silica gel with diethyl ether/hexane/triethylamine; the product-containing fractions are combined and concentrated by evaporation.

Yield: 15.7 g (67% of theory) of colorless oil.
Analysis (relative to solventless substance):
Cld: C 73.37 H 7.70 N 4.28 O 14.66 Fnd: C 73.25 H 7.84 N 4.16 j) N-Benzyl-2-(4-hydroxybenzyl)-3-azaglutaric acid-di-tert-butyl ester 15.1 g (46.1 mmol) of N-benzyl-tyrosine-tert-butyl ester (Example i) is dissolved in 50 ml of tetrahydrofuran and mixed with 5 ml of water and 9.54 g (69 mmol) of potassium carbonate. After instillation of 9.89 g (51 mmol) of bromoacetic acid-tert-butyl ester, it is stirred for two days at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 14.9 g (73.3% of theory) of colorless oil.
Analysis (relative to solventless substance):
Cld: C 74.33 H 8.22 N 3.94 O 13.50 Fnd: C 74.27 H 8.26 N 3.74 k) N-Benzyl-2-(4-ethoxybenzyl)-3-azaglutaric acid-di-tert-butyl ester 13.2 g (30 mmol) of N-benzyl-2-(4-hydroxybenzyl)-3-azaglutaric acid-di-tert-butyl ester (Example j) is dissolved in 50 ml of anhydrous N,N-dimethylformamide and mixed at 0° C. under argon with 1.31 g (33 mmol) of sodium hydride dispersion (60% in mineral oil). The batch is allowed to stir for 15 minutes, then 8.05 g (51.7 mmol) of ethyl iodide is added, the reaction temperature is allowed to increase to room temperature and it is stirred for another three hours. For working-up, the batch is taken up in toluene and shaken out several times against aqueous sodium bicarbonate solution. The organic phase is separated, dried on magnesium sulfate, filtered and concentrated by evaporation. The oily residue is chromatographed for purification on silica gel with hexane/diethyl ether/triethylamine. The product fractions are concentrated by evaporation in a vacuum and dried.

Yield: 12.7 g (90.3% of theory) of colorless oil.
Analysis (relative to solventless substance):
Cld: C 71.61 H 8.37 N 2.98 O 17.03 Fnd: C 71.72 H 8.43 N 2.87 l) 2-(4-Ethoxybenzyl)-3-azaglutaric acid-di-tert-butyl ester 14.2 g (30.2 mmol) of the compound produced according to Example k) is dissolved in 75 ml of ethanol, and after the addition of 1.4 g of palladium (10%) on activated carbon, it is hydrogenated under hydrogen atmosphere at room temperature until hydrogen absorption is completed. After filtration and concentration by evaporation of the filtrate in a vacuum, a colorless oil is obtained.

Yield: 11.3 g (98.6% of theory)
Analysis (relative to solventless substance):
Cld: C 66.46 H 8.77 N 3.69 O 21.08 Fnd: C 66.44 H 8.63 N 3.57 m) 3,6,9-Triaza-3,6-bis-(tert-butoxycarbonylmethyl)-2-(4-ethoxybenzyl)-9,9-bis-[2-(4-methoxyphenyl)-1-((1-methylethoxy)-carbonyl)-ethyl]-nonanoic acid-tert-butyl ester 6.85 g (9.49 mmol) of the compound produced according to Example h) and 3.60 g (9.49 mmol) of the compound described in Example l) are introduced into 15 ml of acetonitrile and mixed with 7.5 ml of 2N phosphate buffer solution (pH 8.0). The batch is vigorously stirred at room temperature for 22 hours, and the aqueous phosphate buffer phase is exchanged for fresh buffer solution after 2 and 7 hours. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 6.26 g (64.6% of theory) of colorless oil.
Analysis (relative to solventless substance):
Cld: C 67.10 H 8.40 N 4.12 O 20.38 Fnd: C 67.21 H 8.54 N 4.17 n) Holmium complex of the disodium salt of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid 6.11 g (5.99 mmol) of the compound produced according to Example m) is dissolved in 20 ml of tetrahydrofuran and mixed with 24 ml of 2N sodium hydroxide solution, it is stirred for two hours at 60° C., adjusted to pH 1 with concentrated hydrochloric acid, greatly concentrated by evaporation in a rotary evaporator and the residue is purified by ion exchange chromatography (cationic exchanger (H$^+$ form), eluent: ammonia-water solution). The eluate is concentrated by evaporation and greatly dried under high vacuum, by which the free complexing agent is obtained. The penta acid is taken up in 250 ml of water and mixed with 1.13 g (2.99 mmol) of holmium oxide. The suspension is stirred for 16 hours at 100° C. and filtered. Then, it is adjusted to pH 7.3 with 1N sodium hydroxide solution. Then, after the addition of 0.6 g of activated carbon, the solution is stirred at 80° C. for one hour and filtered. After freeze-drying, the filtrate yields a colorless solid.

Yield: 5.55 g (95.3% of theory)
Analysis (relative to anhydrous substance):
Cld: C 48.11 H 4.56 N 4.32 O 21.36 Ho 16.94 Na 4.72
Fnd: C 48.12 H 4.64 N 4.21 Ho 16.76 Na 4.55

Example 7

Erbium complex of the disodium salt of 3,6,9-triaza-3,6,9-tris-(carboxymethyl)-2,10-bis-(4-ethoxybenzyl)-4,8-bis-(4-propoxybenzyl)-undecanedioic acid a) α-Oxo-4-ethoxyphenylacetic acid-propyl ester 10.4 g (50 mmol) of α-oxo-4-ethoxyphenylacetic acid (Bandyopahyay et al., J. Ind. Chem. Soc. 66(4), 239, 1989) and 1.0 g of p-toluenesulfonic acid-monohydrate are refluxed into a mixture of 100 ml of toluene and 50 ml of N-propanol while in a water separator until no more water separates out. Then, it is concentrated by evaporation in a vacuum, the residue is dispersed between ethyl acetate and sodium bicarbonate solution, the organic phase is dried on magnesium sulfate, filtered and concentrated by evaporation.

Yield: 10.9 g (87.3% of theory) of yellowish oil.
Analysis (relative to solventless substance):
Cld: C 67.18 H 7.25 O 25.57 Fnd: C 67.33 H 7.32 b) 3-Aza-2-(4-ethoxybenzyl)-5-hydroxy-4-(4-propoxybenzyl)-valeric acid-propyl ester 10.1 g (40.4 mmol) of the compounds described in Example a) and 8.44 g (40.4 mmol) of the compounds described in Example 4c) are stirred in 80 ml of methanol for two hours at 50° C. Then, 0.76 g (20.2 mmol) of sodium borohydride is added in portions at 0° C. It is allowed to stir overnight and then the reaction mixture is carefully mixed with diluted hydrochloric acid until no more gas generation can be observed. The reaction mixture is concentrated by evaporation and the residue is dispersed between ethyl acetate and sodium bicarbonate solution, the organic phase is dried on sodium sulfate, filtered and concentrated by evaporation. The residue is chromatographed on silica gel with use of hexane/ethyl acetate as mobile solvent. The fractions that contain the pure product are combined and concentrated by evaporation.

Yield: 14.1 g (78.7% of theory) of pale yellow oil.
Analysis (relative to solventless substance):
Cld: C 70.40 H 8.41 N 3.16 O 18.03 Fnd: C 70.28 H 8.53 N 3.17 c) 3-Aza-2-(4-ethoxybenzyl)-5-hydroxy-4-(4-propoxybenzyl)-3-(tert-butoxycarbonylmethyl)-valeric acid-propyl ester 13.6 g (30.7 mmol) of the compound described under Example b) is dissolved in 150 ml of toluene. 4.24 g (30.7 mmol) of powdered potassium carbonate and 6.58 g (33.7 mmol) of bromoacetic acid-tert-butyl ester are added and stirred until the reaction is completed at an internal temperature of 70° C. Then, it is filtered, concentrated by evaporation, and the residue is chromatographed on silica gel with hexane/ethyl acetate. The fractions that contain the pure product are combined and concentrated by evaporation in a vacuum.

Yield: 12.4 g (72.6% of theory) of yellowish oil.
Analysis:
Cld: C 68.91 H 8.49 N 2.51 O 20.08 Fnd: C 70.06 H 8.55 N 2.24 d) 3-Aza-5-bromo-2-(4-ethoxybenzyl)-4-(4-propoxybenzyl)-3-(tert-butoxycarbonylmethyl)-valeric acid-propyl ester A solution of 12.0 g (21.5 mmol) of the compound described under c) and 6.21 g (23.7 mmol) of triphenylphosphine in 70 ml of dichloromethane is mixed at 0° C. in portions with 4.21 g (23.7 mmol) of N-bromosuccinimide and then stirred for 20 hours at room temperature. The solution is concentrated by evaporation and the residue is absorptively precipitated with hexane. A precipitate develops, which is separated and washed with hexane. The combined filtrates are concentrated by evaporation and the residue is chromatographed on silica gel with hexane/diethyl ether. The concentration by evaporation of the product fractions yields a colorless oil.

Yield: 10.9 g (81.4% of theory) of colorless oil.
Analysis (relative to solventless substance):
Cld: C 61.93 H 7.47 Br 12.88 N 2.26 O 15.47 Fnd: C 62.14 H 7.31 Br 12.69 N 2.42 e) 3,6,9-Triaza-3,6,9-tris-(tert-butoxycarbonylmethyl)-2,10-bis-(4-ethoxybenzyl)-4,8-bis-(4-propoxybenzyl)-undecanedioic acid-dipropyl ester 10.5 g (16.9 mmol) of the compound produced according to Example d) and 1.11 g (8.46 mmol) of glycine-tert-butyl ester are introduced into 30 ml of acetonitrile and mixed with 15 ml of 2N phosphate buffer solution (pH 8.0). The batch is vigorously stirred at room temperature for 22 hours, and the aqueous phosphate buffer phase is exchanged for fresh buffer solution after 2 and 7 hours. Then, the organic phase is concentrated by evaporation in a vacuum and the residue is chromatographed on silica gel with hexane/ethyl acetate/triethylamine. The product-containing fractions are concentrated by evaporation in a vacuum.

Yield: 6.83 g (66.7% of theory) of colorless oil.
Analysis (relative to solventless substance):
Cld: C 69.45 H 8.58 N 3.47 O 18.50 Fnd: C 69.27 H 8.50 N 3.59 f) Erbium complex of the disodium salt of 3,6,9-triaza-3,6,9-tris-(carboxymethyl)-2,10-bis-(4-ethoxybenzyl)-4,8-bis-(4-propoxybenzyl)-undecanedioic acid 6.64 g (5.48 mmol) of the compound produced according to Example e) is dissolved in 20 ml of tetrahydrofuran and mixed with 24 ml of 2N sodium hydroxide solution, it is stirred for two hours at 60° C., adjusted to pH 1 with concentrated hydrochloric acid, greatly concentrated by evaporation in a rotary evaporator and the residue is purified by ion exchange chromatography (cationic exchanger (H+ form), eluent: ammonia-water solution). The eluate is concentrated by evaporation and greatly dried under high vacuum, by which the free complexing agent is obtained.

The penta acid is taken up in 250 ml of water and mixed with 1.04 g (2.74 mmol) of erbium oxide. The suspension is stirred for 16 hours at 100° C. and filtered. Then, it is adjusted to pH 7.3 with 1N sodium hydroxide solution. Then, after the addition of 0.6 g of activated carbon, the solution is stirred at 80° C. for one hour and filtered. After freeze-drying, the filtrate yields a colorless solid.

Yield: 5.78 g (90.3% of theory)
Analysis (relative to anhydrous substance):
Cld: C 53.55 H 5.36 N 3.60 O 19.20 Er 14.34 Na 3.94
Fnd: C 53.63 H 5.42 N 3.51 Er 14.21 Na 3.77

Example 8

Study of acute toxicity ($LD_{50}$) after one-time intravenous administration to mice The contrast medium to be tested was administered to the mice in individual restraining cages (strain: NMRI (SPF); cultivator: Schering; average weight: 20 g; same sex distribution) into one of the caudal veins at a rate of 2 ml/minutes and at different dosage levels. The number of animals that died up to a fixed time was determined (3 hours, 24 hours, 3 days and 7 days).

The $LD_{50}$ for the ytterbium complex according to Example 2e is approximately 15 mmol/kg of body weight.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula I

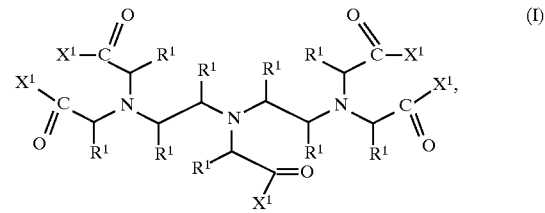

wherein
$R^1$ is, in each case, H or a radical of formula Ia

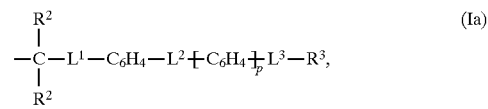

in which 5, 6 or 7 of the $R^1$ groups are each H and the other $R^1$ groups, independently of one another, are each a radical of formula Ia;

p is 0 or 1;

$R^2$ is, in each case independently of one another, H or a branched or unbranched, saturated or unsaturated $C_1$–$C_6$ hydrocarbon radical;

$R^3$ is H, carboxyl, or a branched or unbranched, saturated or unsaturated $C_1$–$C_6$ hydrocarbon radical;

$L^1$ is a direct bond, a sulfur atom, a $C_1$–$C_4$ alkylene chain or a $C_1$–$C_4$ alkylene chain that is interrupted by a sulfur atom;

$L^2$ and $L^3$ are, each independently of one another, a direct bond, an oxygen atom, a sulfur atom, a $C_1$–$C_{10}$ alkylene chain, or a $C_{1-10}$-alkylene chain interrupted by one to three oxygen atoms and/or one to three sulfur atoms, wherein in $L^2$—$[C_6H_4]$—$L^3$ two or more heteroatoms are not directly bonded to one another;

$X^1$ is, in each case independently of one another, O—$X^2$ or N($R^4$)$R^5$;

$R^4$ and $R^5$ are each, independently of one another, H, $C_1$–$C_6$ alkyl or a $R^1$ group, $R^4$ and $R^5$ also can together, with inclusion of the common amide nitrogen atom, form a four- to eight-membered ring, which can in addition, optionally contain 1–2 oxygen atoms and/or 1–2 carbonyl or sulfonyl groups;

$X^2$ is, in each case independently of one another, H or a metal ion equivalent of an element of atomic numbers 20-32, 39-51 or 57-83; or a salt thereof with a physiologically compatible inorganic and/or organic cations.

2. A compound according to claim 1, wherein all $X^1$ groups are O—$X^2$.

3. A compound according to claim 1, wherein one or two $X^1$ groups are each a N($R^4$)$R^5$ group.

4. A compound according to claim 1, wherein at least two $X^2$ groups are metal ion equivalents of an element of atomic numbers 20-32, 39-51 or 57-83.

5. A compound according to claim 1, wherein all $X^2$ groups are H.

6. A compound according to claim 1, wherein said compound contains contain sodium, calcium, magnesium, zinc, meglumine, glucosamine, arginine, ornithine, lysine and/or ethanolamine ions as physiologically compatible cations.

7. A compound according to claim 1, wherein at least one of the $R^1$ groups is methoxybenzyl, ethoxybenzyl, propoxybenzyl, butoxybenzyl, pentoxybenzyl, ethoxyethoxybenzyl, 2-(2-ethoxyethoxy)-ethoxybenzyl, benzyloxybenzyl, methylbenzyl, ethylbenzyl, propylbenzyl, butylbenzyl, pentylbenzyl or benzylbenzyl.

8. A compound according to claim 1, wherein two $R^1$ groups are each a radical of formula Ia.

9. A compound according to claim 1, wherein two $R^1$ groups are each ethoxybenzyl.

10. A compound according to claim 1, wherein three $R^1$ groups are each a radical of formula Ia.

11. A compound according to claim 1, wherein three $R^1$ groups are each ethoxybenzyl.

12. A compound according to claim 1, wherein four $R^1$ groups are each ethoxybenzyl.

13. A compound according to claim 1, wherein said compound is:

3,6,9-triaza-3,9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid or a salt thereof with physiologically acceptable cations;

3,6,9-triaza-3,6,9-tris-(carboxymethyl) -4,8-bis-(4-ethoxybenzyl)-undecanedioic acid or a salt thereof with physiologically acceptable cations;

3,6,9-triaza-3,6,9-tris-(carboxymethyl)-2,10-bis-(4-ethoxybenzyl)-undecanedioic acid or a salt thereof with physiologically acceptable cations;

3,6,9-triaza-3,9-bis-(carboxymethyl)-6-{2-[4-(carboxymethoxy)-phenyl]-1-carboxyethyl}-4-[4-propoxybenzyl]-undecanedioic acid or a salt thereof with physiologically acceptable cations;

3,6,9-triaza-6-(carboxymethyl)-3,9-bis-[2-(4-methoxyphenyl)-1-carboxyethyl]-2,10-bis-(4-methoxybenzyl)-undecanedioic acid or a salt thereof with physiologically acceptable cations;

3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid or a salt thereof with physiologically acceptable cations;

3,6,9-triaza-3,6,9-tris-(carboxymethyl)-2,10-bis-(4-ethoxybenzyl)-4,8-bis-(4-propoxybenzyl)-undecanedioic acid or a salt thereof with physiologically acceptable cations;

bismuth complex of 3,6,9-triaza-3,9-bis-(carboxymethyl)-6-{2-[4-(1,4,7-trioxaoctyl)-phenyl]-1-carboxyethyl}-4,8-bis-[4-(1,4,7-trioxaoctyl)-benzyl]-undecanedioic acid or a salt thereof with physiologically acceptable cations;

ytterbium complex of 3,6,9-triaza-3,6,9-tris-(carboxymethyl)-4,8-bis-(4-ethoxybenzyl)-undecanedioic acid or a salt thereof with physiologically acceptable cations;

gadolinium complex of 3,6,9-triaza-3,6,9-tris-(carboxymethyl)-2,10-bis-(4-ethoxybenzyl)-undecanedioic acid or a salt thereof with physiologically acceptable cations;

hafnium complex of 3,6,9-triaza-3,9-bis-(carboxymethyl)-6-{2-[4-(carboxymethoxy)-phenyl]-1-carboxyethyl}-4-[4-propoxybenzyl]-undecanedioic acid or a salt thereof with physiologically acceptable cations;

terbium complex of 3,6,9-triaza-6-(carboxymethyl)-3,9-bis-[2-(4-methoxyphenyl)-1-carboxyethyl]-2,10-bis-(4-methoxybenzyl)-undecanedioic acid or a salt thereof with physiologically acceptable cations;

holmium complex of 3,6,9-triaza-6,9-bis-(carboxymethyl)-3-[(4-methoxybenzyl)-carboxymethyl]-10-(4-ethoxybenzyl)-2-(4-methoxybenzyl)-undecanedioic acid or a salt thereof with physiologically acceptable cations; or erbium complex of 3,6,9-triaza-3,6,9-tris-(carboxymethyl)-2,10-bis-(4-ethoxybenzyl)-4,8-bis-(4-propoxybenzyl)-undecanedioic acid or a salt thereof with physiologically acceptable cations.

14. A compound according to claim 1, wherein said compound contains a paramagnetic metal.

15. A compound according to claim 1, wherein said compound contains a radioactive metal.

16. A compound according to claim 1, wherein said compound contains a metal of the lanthanide series.

17. A compound according to claim 16, wherein said metal is gadolinium, dysprosium, holmium, erbium, terbium or ytterbium.

18. A compound according to claim 1, wherein said compound contains bismuth, lead or hafnium.

19. A compound according to claim 14, wherein said metal is manganese or iron.

20. A compound according to claim 15, wherein said metal is gallium, indium or technetium.

21. A compound according to claim 1, wherein said compound contains calcium or zinc.

22. A pharmaceutical agent comprising at least one physiologically compatible compound according to claim 1, a physiologically acceptable carrier, and optionally one or more galenic additives.

23. In a method of performing diagnostic radiology imaging comprising administering a contrast agent, the improvement wherein said agent comprises at least one physiologically compatible compound according to claim 1, wherein said compound is a chelate complex.

24. In a method of performing NMR imaging comprising administering a contrast agent, the improvement wherein said agent comprises at least one physiologically compatible compound according to claim 14.

25. In a method of performing radiodiagnostic imaging comprising administering a contrast agent, the improvement wherein said agent comprises at least one physiologically compatible compound according to claim 15.

26. In a method of performing diagnostic radiology imaging, NMR imaging and/or radiodiagnostic imaging comprising administering a contrast agent, the improvement wherein said agent comprises at least one physiologically compatible compound according to claim 1, wherein said compound is a chelate complex and imaging of the liver, the gallbladder and/or the bile ducts is performed.

27. A method according to claim 26, wherein diagnosis by computer tomography of the liver, the gallbladder and/or the bile ducts is performed.

28. In a method of performing radiotherapy comprising administering a contrast agent, the improvement wherein said agent comprises at least one physiologically compatible compound according to claim 15.

29. In a method of removal of undesirable heavy metals from an organism comprising administering a contrast agent, the improvement wherein said agent comprises at least one physiologically compatible compound according to claim 1.

30. A method according to claim 29, wherein undesirable heavy metals are removed from the liver.

31. A compound of formula I

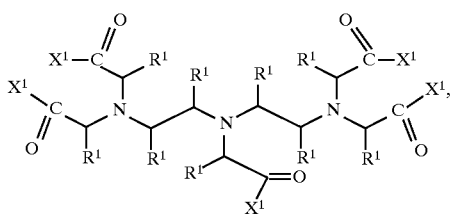

wherein $R^1$ is, in each case, H or a radical of formula Ia

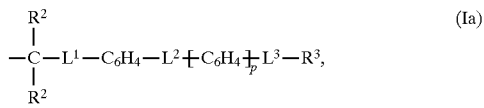

in which 2, 3 or 4 of the $R^1$ groups are each independently a radical of formula Ia and the other $R^1$ groups are each H;

p is 0 or 1;

$R^2$ is, in each case independently of one another, H or a branched or unbranched, saturated or unsaturated $C_1$–$C_6$ hydrocarbon radical;

$R^3$ is H, carboxyl, or a branched or unbranched, saturated or unsaturated $C_1$–$C_6$ hydrocarbon radical;

$L^1$ is a direct bond, a sulfur atom, a $C_1$–$C_4$ alkylene chain or a $C_1$–$C_4$ alkylene chain that is interrupted by a sulfur atom;

$L^2$ and $L^3$ are, each independently of one another, a direct bond, an oxygen atom, a sulfur atom, a $C_1$–$C_{10}$ alkylene chain, or a $C_{1\text{-}10}$-alkylene chain interrupted by one to three oxygen atoms and/or one to three sulfur atoms, wherein in $L^2$—[$C_6H_4$]—$L^3$ two or more heteroatoms are not directly bonded to one another;

$X^1$ is, in each case independently of one another, O—$X^2$ or $N(R^4)R^5$;

$R^4$ and $R^5$ are each, independently of one another, H, $C_1$–$C_6$ alkyl or a $R^1$ group, $R^4$ and $R^5$ also can together, with inclusion of the common amide nitrogen atom, form a four- to eight-membered ring, which can in addition, optionally contain 1–2 oxygen atoms and/or 1–2 carbonyl or sulfonyl groups;

$X^2$ is, in each case independently of one another, H or a metal ion equivalent of an element of atomic numbers 20-32, 39-51 or 57-83; or a salt thereof with a physiologically compatible inorganic and/or organic cations.

32. A compound according to claim 1, wherein $R^4$ and $R^5$ are each, independently of one another, H, $C_1$–$C_6$ alkyl; and $R^4$ and $R^5$ also can together, with inclusion of the common amide nitrogen atom, form a four- to eight-membered ring, which can in addition, optionally contain 1–2 oxygen atoms and/or 1–2 carbonyl or sulfonyl groups.

33. A compound according to claim 31, wherein $R^4$ and $R^5$ are each, independently of one another, H, $C_1$–$C_6$ alkyl; and $R^4$ and $R^5$ also can together, with inclusion of the common amide nitrogen atom, form a four- to eight-membered ring, which can in addition, optionally contain 1–2 oxygen atoms and/or 1–2 carbonyl or sulfonyl groups.

* * * * *